United States Patent [19]

Beaumont

[11] 4,094,773
[45] June 13, 1978

[54] PROCESS FOR SEWAGE TREATMENT WITH COUNTERCURRENT HEAT TRANSFER MEANS

[76] Inventor: Stanley Beaumont, 118 Macorna St., Watsonia, Australia

[21] Appl. No.: 761,859

[22] Filed: Jan. 24, 1977

Related U.S. Application Data

[60] Division of Ser. No. 667,171, Mar. 15, 1976, which is a continuation-in-part of Ser. No. 603,623, Aug. 11, 1975, abandoned, which is a continuation of Ser. No. 435,647, Jan. 23, 1974, abandoned.

[51] Int. Cl.$^2$ .............................................. C02C 1/06
[52] U.S. Cl. ...................................... 210/5; 210/12; 210/16
[58] Field of Search ............ 210/211, 16, 12, 181–183, 210/256, 301, 5, 8

[56] References Cited

U.S. PATENT DOCUMENTS

| | | |
|---|---|---|
| 1,963,581 | 6/1934 | Heukelekian .......................... 210/12 |
| 2,315,577 | 4/1943 | Bach ....................................... 210/12 |
| 2,430,519 | 11/1947 | Mallory ................................. 210/256 |
| 3,395,799 | 8/1968 | Kurtz ..................................... 210/12 |
| 3,462,275 | 8/1969 | Bellamy ................................. 210/11 |
| 3,694,353 | 9/1972 | Yong et al. ............................ 210/256 |
| 3,745,113 | 7/1973 | Fuchr ..................................... 210/12 |

Primary Examiner—Thomas G. Wyse
Attorney, Agent, or Firm—Depaoli & O'Brien

[57] ABSTRACT

Apparatus and method are disclosed for an anaerobic process in three stages having progressively higher temperatures up to 75° C. for digesting raw household sewage with methane forming bacteria, in which dolomite is added to control the pH of the system within the range 6.0–7.5. After a sterilization fourth stage at 82° C. or greater, the effluent is treated in a ground filter. Heat is countercurrently transferred from the sterilization stage effluent to the substrate of the digestion stages. The apparatus for carrying out this process has an underlying heat-exchange compartment and four concentric compartments, of which the innermost is the sterilization stage compartment containing a heating means and the outermost compartments are flow chambers for sequentially digesting the sewage in psychrophilic, mesophilic, and thermophilic stages, prior to sterilizing. The thermophilic stage contains a micron-size filter upon which a bacterial slime forms and which passes a sediment-free, treated effluent. Sterilized effluent from the fourth stage passes through the underlying heat-exchange compartment having the form of a truncated cone for heat exchange to the bottoms of the three concentric flow chambers.

8 Claims, 6 Drawing Figures

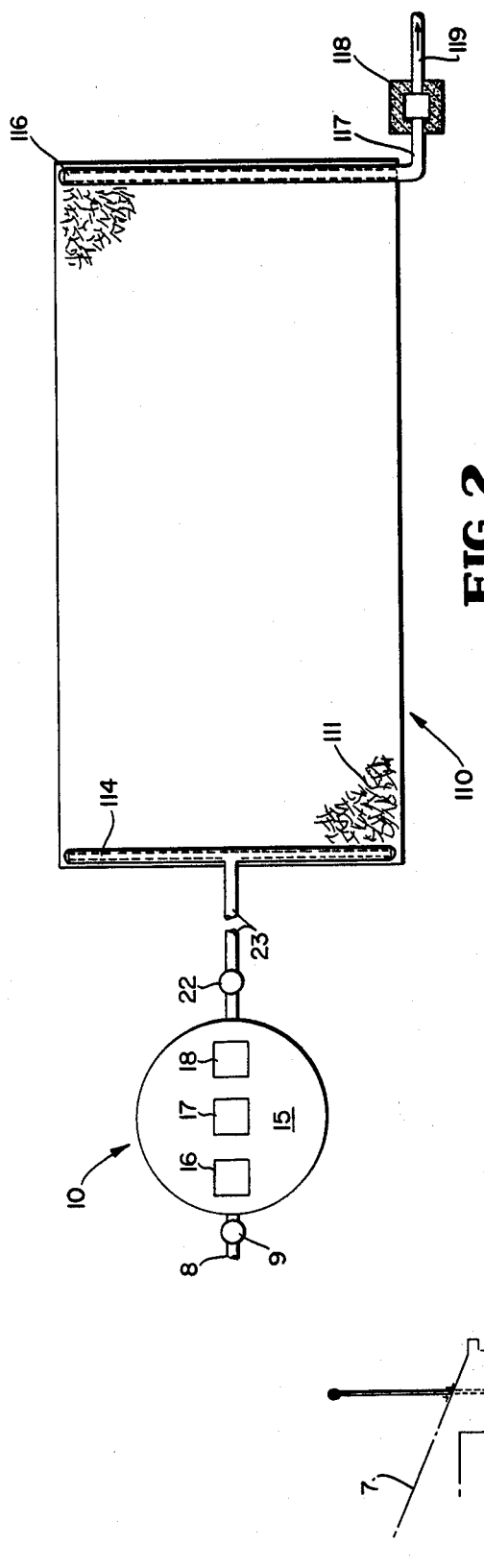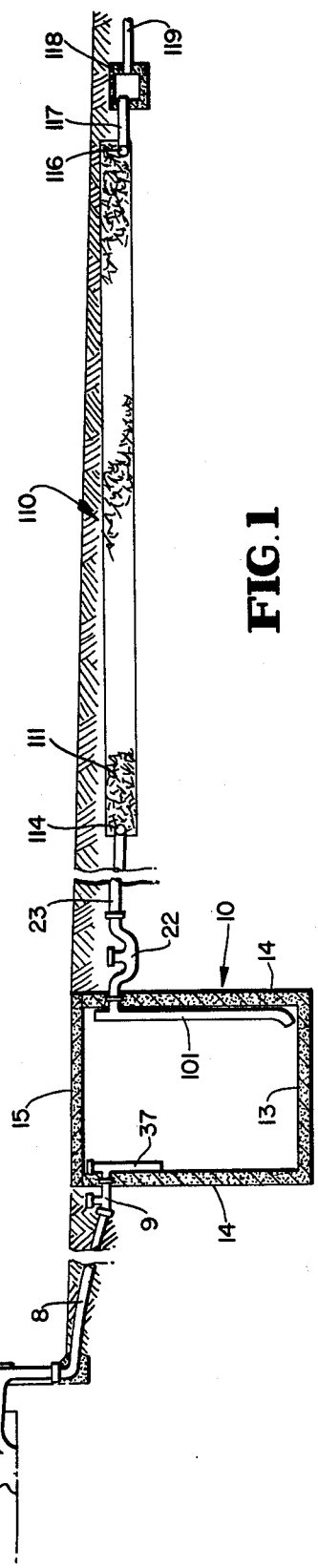

FIG. 3
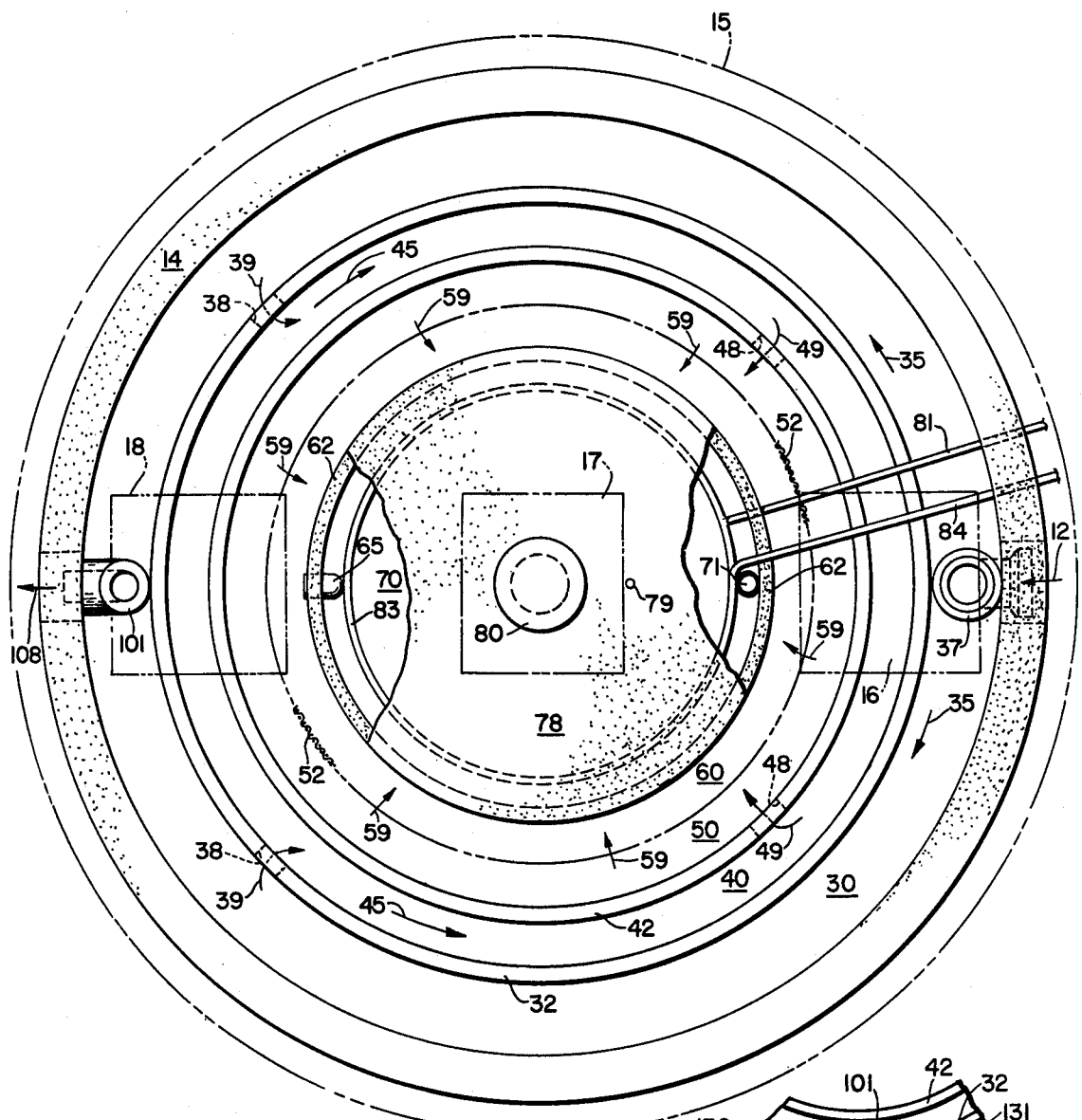
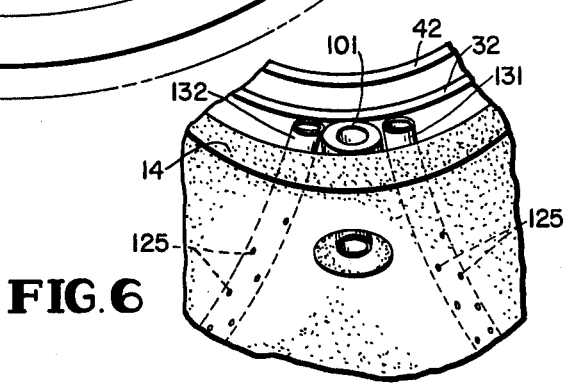
FIG. 5
FIG. 6

PROCESS FOR SEWAGE TREATMENT WITH COUNTERCURRENT HEAT TRANSFER MEANS

This is a divisional application of application Ser. No. 667,171, filed Mar. 15, 1976, which is a continuation-in-part of Application Ser. No. 603,623, filed Aug. 11, 1975 and now abandoned, which is a continuation of Ser. No. 435,647, filed Jan. 23, 1974 and now abandoned.

BACKGROUND OF THE INVENTION

1. Field of the Invention

This invention relates to processes and apparatus for digesting aqueous organic materials, such as sewage from household and municipal sources, or industrial or trade wastes. It particularly relates to anaerobic digestion thereof at elevated temperatures.

2. Review of the Prior Art

The anaerobic digestion of aqueous organic materials is considered to consist of the reactions occurring in series as illustrated below and as discussed by John F. Andrews in "Control Strategies for the Anaerobic Digestion Process, Part I" in Water and Sewage Works, March, 1975.

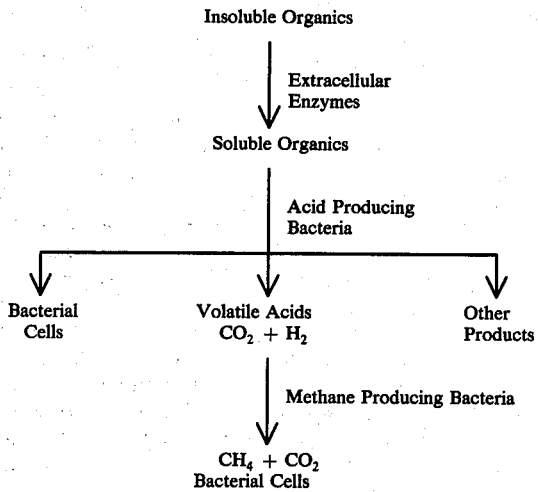

It may be seen that the anaerobic digestion process actually occurs in two general steps: (1) the acid fermentation stage and (2) the methane fermentation stage.

In the second stage, highly obligate anaerobes, collectively known as methane formers, are required. The presence of any free or dissolved oxygen will destroy or at least severely inhibit further digestion because of the oxygen-sensitivity of the methane formers. A true anaerobic system must not contain any available or free oxygen; chemical oxygen alone is used in the oxidation-reduction reactions. A free oxygen content as low as 0.08 ppm is lethal to many of the true or obligate anaerobes.

The Andrews article (supra) reveals that the acid-producing bacteria are less susceptible than the methane bacteria to changes in environmental conditions such as pH, temperature, and inhibitory substances. Moreover, because most species of methane bacteria have much lower growth rates than the acid producing bacteria, the rate-limiting step in the overall anaerobic digestion process is the conversion by the methane bacteria of the intermediate products (i.e., the volatile acids and carbon dioxide produced by the acid producing bacteria) to methane and carbon dioxide. It is also known that acetic acid is the precursor of approximately 70% of the methane produced in the digestion of organic sludges from municipal waste water treatment plants. The specific growth rate for methane bacteria was shown by Andrews to be significantly inhibited by decreasing pH, particularly with total substrate concentrations beyond about 20 millimoles per liter.

Obviously, methane formers that cannot exist outside of their particular pH, temperature, and true anaerobic condition could not conceivably be present in present-day sludge digestors or extended aeration trickling filters or septic tanks. Sludge digestors that operate at a normally fixed temperature of 24°-28° C clearly exclude most of the essential methane formers and required pH ranges.

United States Pat. No. 1,963,581 teaches the organisms in ordinary sludge digestion are most active at temperatures between 16° C and 20° C and are killed at temperatures of 49° C to 60° C which are best for growth of facultative thermophiles and obligate thermophiles. These thermophiles are also most active in sludge digestion within the pH range of 7.8-8.2. Some of the bacteria in the thermophilic group are liquifying bacteria which provide food from cellulosic material for gasifying bacteria so that it was thought that an insufficiency of liquifying bacteria could cause a shortage of food for the gasifying bacteria. Lime was added to the sludge to produce food that would be directly available to the gasifying bacteria, i.e., organic salts such as calcium acetate, thereby rendering the gasifying bacteria independent of the liquifying bacteria. In addition the sludge was heated to temperatures ranging between 45° C and 70° C to destroy the major portion of the bacteria active at lower temperatures by stimulating the reproduction of and activity of thermophilic bacteria, thereby increasing gas production and greatly shortening the time required by digestion of the sludge.

It is shown in the prior art that anaerobic digestion processes can be doubled in rate for each 10° C rise in temperature between 10° C and 60° C, thereby reducing the time required for digesting from six months at the lower temperature range to 12 days at 60° C. Accordingly, a sludge digestor is described in U.S. Pat. No. 2,430,519 for digestion of sludges and similar highly concentrated wastes in subsequent stages having successively lower temperatures, the initial stage of digestion being at a temperature of about 102°-108° F (38.9°-42.2° C). Another sludge treatment is described in U.S. Pat. No. 2,188,847, wherein sludge is heated at the bottom of a deep tank having a central convection tube.

Although sludge digestors are normally considered to be anaerobic units, they are not treatment plants but are means for considerably reducing high concentrations of organic wastes which are accumulated in treatment plants. The substrate of such digestors have 5-day biological oxygen demands in the order of 20,000 ppm or greater. The more prevalent type of anaerobic unit, which is not properly considered a treatment plant, is the septic tank.

In the United States, census figures show that approximately one-third of the population is served by individual household treatment systems for waste water disposal. In 1970 there were approximately 17 million septic tank systems, and such septic tank soil absorption systems will continue to be used for some time in the future. The coliform count of the effluent from typical septic tanks may be higher than one million per milliliter, a number which is 10,000 times the permissible level of the recommended 1968 standards for surface water used for bathing. Typically, septic tanks remove about 50% of chemical oxygen demand (COD), about 50% of the biochemical oxygen demand (BOD), and about 75% of the suspended solids of the untreated effluent.

Normal household septic tanks are usually cylindrical or rectangular concrete structures of 400 gallon capacity in which household wastes are treated at ambient temperatures only. No attempt is made, other than occasional liming, to control the pH. The effluent is passed through crushed stone filter drains for further biological treatment and absorption. Unfortunately, the interstitial spaces of the drains and soil become clogged with sewage solids, resulting in localized ponding that causes foul odors and health hazards. Such effluent can be expected to be in the range of 12–1,400 ppm of biological oxygen demand over five days ($BOD_5$), 1,800–2,000 ppm of suspended solids, and $1 \times 10^8$/ml.° C of ESCHERICHIA coliform organisms.

Recognizing the methane fermentation stage to be the rate limiting step of the anaerobic digestion process, suggestions have been advanced in the art to accelerate the reaction rates of that step. For example, Pohland and Ghosh have proposed a two-phase anaerobic digestion process in which the acid and methane formers were provided with optimum environments in separate acid and methane fermentation reactors connected in series ("Developments in Anaerobic Treatment Processes", *Biological Waste Treatment*, Wiley Interscience Publishers, New York, New York (1971), at page 85; "Anaerobic Stabilization of Organic Wastes-Two-Phase Concept", *Environmental Letters*, April, 1971, at page 255). Also, Borchardt described a dialysis technique in which the acid- and methane fermentations were separated into separate chambers ("Anaerobic Phase Separation by Dialysis Technique", Advanced Chemistry Ser., 105, 108 (1971)). The fastidious methane flora were fed with the products of acid fermentation permeating through a membrane.

Treatment plants presently used for domestic sewage and industrial waste are frequently troubled by foul odors, noise from air-blowers, compressors, pumps, and agitators, and inability to treat underload or overload conditions. Treatment plants for individual households or small groups of households, particularly septic tanks, are not satisfactory because the output therefrom is often ecologically unacceptable. Furthermore, grease traps often used in conjunction with such treatment systems sometimes create obnoxious odors and require frequent cleaning.

Accordingly, there is a need for a sewage treatment plant that is operable without maintenance, without skilled supervision, and without machinery. There is further a need for a sewage treatment plant that can utilize an anaerobic process at elevated temperatures with means for achieving a sequential gradation of temperature. It is further desirable to have an anaerobic process that has a sterilized effluent. It is also important in such an anaerobic process to provide additional means for deodorizing and oxidizing the treated and sterile effluent and then removing the nitrogen so that the fluid can be added to existing waterways without ecological deterioration.

SUMMARY OF THE INVENTION

It is accordingly an object of this invention to provide a process for anaerobic digestion with methanobacteria within stages having sequentially increasing temperature.

It is also an object to provide an anaerobic process having a means for maintaining the pH within the range of 6.0 to 7.5.

It is further an object to provide a means for sterilizing the effluent from the anaerobic digestion process.

It is additionally an object to provide an aerobic digestion step for removing excess nitrogen and odors from the treated and sterile effluent of the anaerobic process.

It is still further an object to provide an apparatus for sequential treatment, automatic heat transfer, accelerated sludge digestion, sterilization, and aerobic treatment following this anaerobic digestion.

In satisfaction of these objects and in accordance with the spirit of this invention, a process and apparatus for treating sewage is herein provided that broadly comprises: (a) an anaerobic system that produces from raw sewage a clear, sterilized product containing nitrogen compounds and (b) an aerobic system that removes the nitrogen compounds and reduces BOD thereof. The anaerobic system has five stages that are carried out in five compartments which are arranged to provide counter-current heat transfer and to produce a clear, sterilized product. The aerobic system has one stage.

The anaerobic system comprises three sequentially operating stages for prolonged digestion of raw sewage at progressively increasing temperatures, so that distinct bacterial species are utilized. Each stage has a bottom zone, a supernatant zone, and a top zone. Along the entire length of the bottom zone of each stage, heat is received, creating convection currents rising through the supernatant zone and the top zone. Operating entirely on a bulk displacement basis, raw sewage enters the first stage and supernatant liquor passes from the supernatant zone of each stage to the next stage. Along the entire lengths of the bottom zones of the first two stages, sludge and slime are countercurrently received from the succeeding stage. The third stage further comprises a micron-size filter, disposed lengthwise therein, that offers a large area upon which a bacterial slime forms and through which a clear product passes. The slime collects thereupon while being digested with methanobacteria, with excess slime dropping to the bottom and sliding sidewise to the bottom of the preceding compartment. The clear product of the third stage passes into a sterilizing fourth stage and then to a heat-transfer fifth stage which is disposed to transfer heat countercurrently to the bottom of each of the first four stages.

The aerobic system comprises a single stage for dispersing the clear, sterilized product from the anaerobic system as a thin film in which it is cooled and aerated so that nitrogen is bacteriologically removed. The final product consequently is clear, free of pathogenic organisms, and low in both nitrates and biochemical-oxygen demand so that it is suitable for discharge to waterways.

More specifically, the process within the anaerobic system comprises:

A. as a psychrophilic stage, flowing raw untreated sewage by gravity within a narrow and deep psychrophilic compartment while:
   (1.) heating the sewage along the bottom of the psychrophilic compartment to create upward convection currents and form thermally stratified bottom, supernatant, and top zones, (2.) receiving transversely moving mesophilic sludge along this bottom from an adjoining narrow and deep mesophilic compartment, and
(3.) digesting the sewage at a temperature of about 20°–45° C to form a psychrophilic sludge and a psychrophilic supernatant;

B. as a mesophilic stage, transferring the psychrophilic supernatant by displacement to the mesophilic compartment and flowing the psychrophilic supernatant therein while:
  (1.) heating the supernatant along the bottom of the mesophilic compartment to create upward convection currents and form thermally stratified bottom, supernatant, and top zones, and
  (2.) receiving transversely moving bacterial slime along the bottom of the mesophilic compartment from an adjoining narrow and deep entrapment portion of a thermophilic compartment; and
  (3.) digesting the psychrophilic supernatant at a temperature of about 35°–55° C to form a mesophilic supernatant and the mesophilic sludge;

C. as a thermophilic stage, transferring the mesophilic supernatant by displacement to the entrapment portion and flowing the supernatant therein while:
  (1.) heatint the supernatant along the bottom of the entrapment portion, to create upward convection currents and form thermally stratified bottom, supernatant, and top zones, and
  (2.) exposing the mesophilic supernatant to a filter which:
    (a) has 50–100 micron apertures, and
    (b) provides sufficient surface area for entrapping any suspended solids greater than 50 microns in size, and
  (3.) digesting the entrapped solids caught on the filter at a temperature of 45°–70° C until the entrapped solids are hydrolyzed and reacted by thermophilic bacteria to form the bacterial slime and a treated fluid and passing the treated fluid through the filter into an adjoining narrow and deep thermophilic treated portion along which the treated fluid flows while being heated along the bottom thereof;

D. as a sterilizing stage, transferring the treated fluid to the bottom zone of a sterilizing compartment having a bottom heat-transfer surface and a heating means;

E. heating the treated fluid from this bottom surface and with the heating means in the sterilizing compartment to form a sterilized treated fluid at the top of the sterilizing compartment;

F. as a heat-exchange stage, transferring the sterilized treated fluid to an underlying storage compartment, having a top area and a sloping side area, from which heat is transferred at successively decreasing temperatures from the top area to the bottom surface of the sterilizing compartment and, from the sloping side area, to the bottoms of the treated and entrapment portions of the thermophilic compartment, the mesophilic compartment, and the psychrophilic compartment; and G. transferring the sterilized treated fluid to an aerobic system for oxidation and de-nitrification.

The apparatus for carrying out the anaerobic system of this invention comprises four side-by-side treatment compartments and one underlying heat-transfer compartment. The treatment compartments are three narrow, deep digestion compartment (the third being divided lengthwise by a micron-size filter into two still narrower hemi-compartments) and one central sterilizing or heat treatment compartment. The het-transfer compartment underlies all four treatment compartments from which it is separated by a heat-conductive material so that each compartment receives heat along the entire length of the bottom thereof.

More specifically, the anaerobic apparatus for carrying out the process of this invention comprises an underlying heat-exchange compartment wherein the sterilized treated fluid is stored for heat transfer. It may be considered a fifth-stage heating means. Thereabove are located the psychrophilic, mesophilic, thermophilic, and sterilizing compartments. The thermophilic compartment is divided by the filter into two hemi-compartments which are termed the thermophilic entrapment portion and the thermophilic treated portion. Preferably, the sterilization fourth compartment is cylindrical and is at the center of the concentric thermophilic, mesophilic, and psychrophilic compartments, the fourth compartment being in the form of a cylinder and the underlying fifth compartment being in the form of a truncated cone. However, a satisfactory apparatus may also be constructed as parallel, adjacent, straight, deep, and narrow flow compartments, which are disposed adjacent and in parallel and have means for countercurrent sidewise transfer of sludge by gravity along the bottoms thereof, and an underlying sterilizing fifth-stage compartment of approximately triangular cross section for upward heat transfer to the four compartments thereabove.

The anaerobic digestion apparatus of this invention essentially comprises a sterilizing cylinder which is placed upright upon the top of a truncated cone, the cross section of the cylinder and of the flat top of the cone being equal. The cylinder is coaxially disposed within a unit container having a base plate. The side wall of the cone extends downwardly as far as the inner perimeter of the unit container and is sealed to the base plate. Two cylindrical baffles are coaxially disposed above and supported upon the side wall of the cone to define three annuli between the outer wall of the unit container and the wall of the sterilizing cylinder. Each of the two baffles is spaced about one inch above the surface of a cone. A cylindrical filter is sealably attached to the side wall of the cone and bisects the inmost annulus.

Ports in the baffles connect the annuli, and a fluid transfer pipe connects the inner portion of the inmost annulus to the bottom of the sterilizing cylinder. Another fluid transfer pipe connects the top of the sterilizing cylinder to the bottom of the cone. A vertically disposed fluid transfer pipe is connected to the lower perimeter of the base of the cone and passes upwardly through the outer annulus, hugging closely to the inner circumference of the outer container and open-endedly terminating about six inches above the top water level within the container. A second water transfer pipe abuts the vertical water transfer pipe at right anles and passes through the outer container about two inches lower than the top water level within the tank. The outer container, the two baffles, the sterilizing cylinder, and the uprightly disposed water transfer pipe are insulated to minimize heat transfer. The cone is constructed of a conductive metal for the purpose of transferring heat from its contents upwardly to the contents of the three annuli and to the central cylinder thereabove.

Even more broadly, the apparatus of this invention can be defined as comprising:
A. three narrow and deep flow chambers which are sequentially interconnected by,
  (1.) fluid transfer means, for forwardly moving supernatant fluid by displacement by sewage entering the apparatus, which are disposed at the ends of each flow chamber and at mid-depth therein and
  (2.) solids transfer means, for countercurrently moving sludge by gravity, which are disposed along the entire lengths of the bottoms thereof;
B. a filter means for entrapping suspended particles, for enabling thermophilic bacteria to digest the entrapped particles, and for permitting clear fluid to pass therethrough;
C. a sterilizing means for heating the clear fluid to temperatures above 75° C., including a heating means for adding heat to the apparatus; and
D. a heat-exchange means for countercurrently transferring heat from the sterilized fluid to the sterilizing means and to the three flow chambers.

Typical outputs from an apparatus constructed according to this invention and operated according to the process described herein are in the range of:

| | |
|---|---|
| 5-day biological oxygen demand, BOD | 8ppm |
| suspended solids | 12ppm |
| *Escharichia Coliform* Organisms | nil |

Maintaining the desired range of pH and temperature for methane formers is absolutely vital because momentary deviation from either the desired temperature or pH ranges will render the system inoperative. These ranges are tabulated as follows for each genus of methane formers from Bergey's "Manual of Determinative Bacteriology", 8th Edition, Williams & Wilkins Co., Baltimore, Maryland, pages 472–477:

| | pH range | Temp. range ° C. |
|---|---|---|
| GENUS I, METHANOBACTERIUM SPECIES | | |
| M/ Bacterium Soehngenii | 6 – 8 | 10 – 35 |
| M/ Bacterium Formicium | 6 – 8 | 38 – 45 |
| M/ Bacterium Thermoautrophicum | 6 ' 8 | 40 – 75 |
| M/ Bacterium Ruminantium | 6 – 8 | 40 – 47 |
| M/ Bacterium Mobile | 5.9 – 7.7 | 30 – 45 |
| GENUS II METHANOSARCINA SPECIES | | |
| Methanosarcina Methanica | approximately 7 | — |
| M/ Sarcina Berkeri | 7 | — |
| GENUS III METHANOCOCCUS SPECIES | | |
| Methanococcus Mazei | 7.4 – 9.2 | 30 – 40 |
| M/Vanniellii | 7 – 9 | 30 – 40 |

In the instant invention, heterotrophic bacteria are used because of their ability to gain all their energy, metabolic needs, and synthetic needs from organic products.

In order to ensure that digestion will not cease because of the pH being depressed to 4.5 or less, dolomite is used in the first stage of the process and compartment apparatus of this invention, thus controlling the pH of the system to the pH range 6.0 to 7.5.

The method and apparatus of this invention is described as applied to sewage from typical domestic premises but it is to be understood that the apparatus and method include the treatment of all organic wastes, whether domestic, industrial, or commercial. Its operation requires no machinery or man-power for period of 3 to 5 years when the treatment plant should be desludged in order to remove the build-up of non-biodegradable end products. Moreover, the power costs of a plant operated according to this invention are small relative to plants discharging an effluent of comparable quality.

BRIEF DESCRIPTION OF THE DRAWINGS

FIG. 1 is an elevation in section of a typical household and of a sewage treatment plant of the invention having both anaerobic and aerobic treatment apparatuses.

FIG. 2 shows the anaerobic and aerobic apparatuses in plan view.

FIG. 3 shows the concentric-type cylindrical anaerobic apparatus of FIGS. 1 and 2 in plan view with the cover removed.

FIG. 5 is a partial top view showing another embodiment of the anaerobic apparatus having means for placing dolomite within and close to the exit from the first compartment.

FIG. 6 is a top perspective view of an embodiment similar to FIG. 5, showing means for placing dolomite within and close to the feed into the first compartment of the anaerobic apparatus.

DESCRIPTION OF THE PREFERRED EMBODIMENTS

Figure 4:
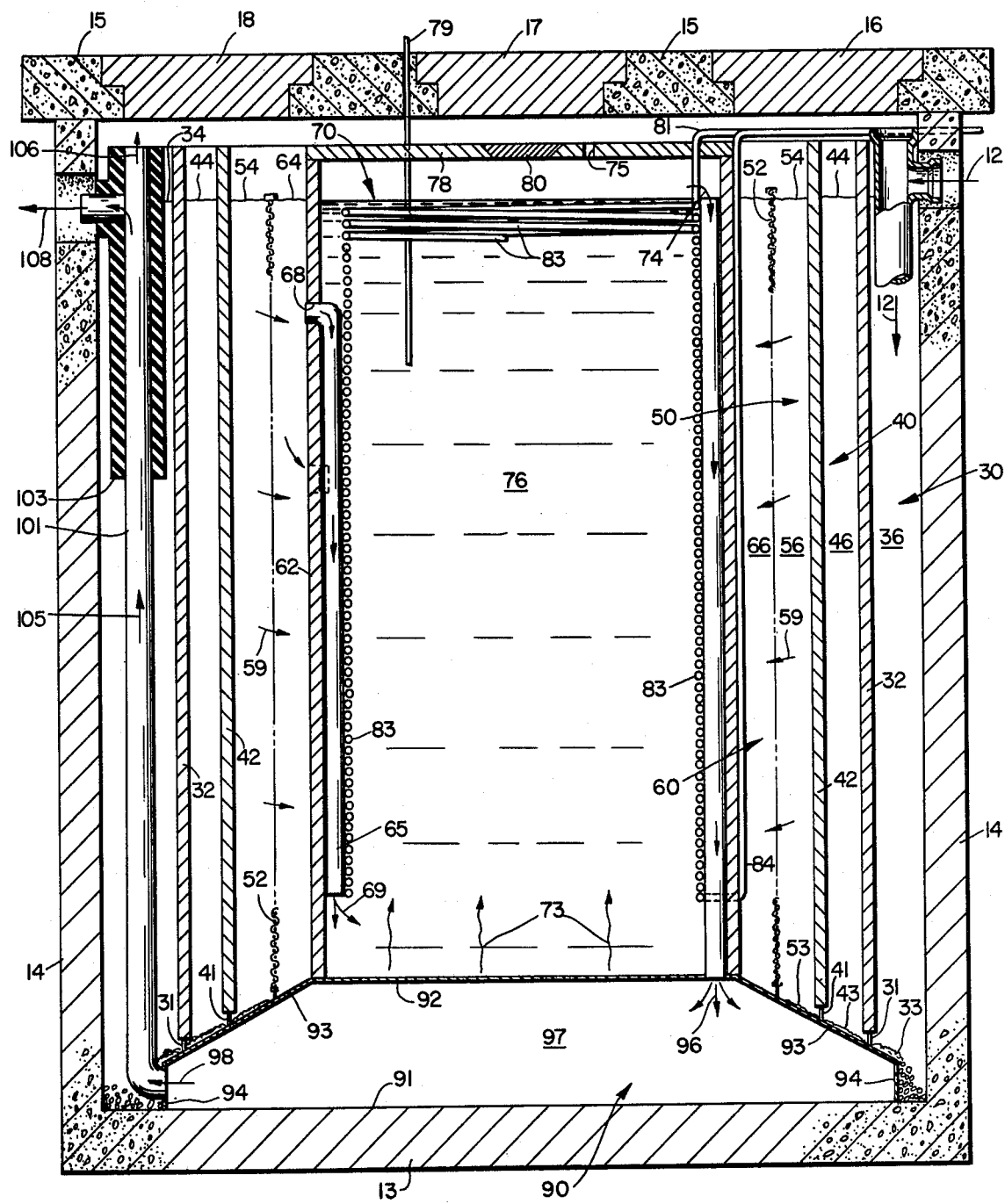
FIG. 4 shows the anaerobic apparatus of FIG. 3 in sectional elevation.

Referring particularly to FIGS. 1 and 2, domestic slurries 12, flow from one or more households 7 through a pipe 8 and tee 9, enters the anaerobic digesting apparatus 10, and departs therefrom through trap 22 and line 23 into the aerobic filter bed 110 of the aerobic apparatus. The apparatus 10 has a concrete exterior with bottom 13, wall 14, and lid 15. Manhole covers 16, 17, and 18 are shown in the lid 15.

The aerobic filter bed 110 is a ground filter constructed in an excavation of considerable area, such as 10 feet by 20 feet, and having a minimum depth of 12 inches; it is as horizontal as possible. The anaerobic apparatus 10 and the aerobic filter bed 110 are interconnected by a boundary trap 22 and a line 23. The trap 22 is a boundary or siphon trap for creating a water trap or seal to prevent air from passing back from the aerobic apparatus to the interior of the anaerobic apparatus and thereby destroying the anaerobic environment thereof.

Referring to FIGS. 3 and 4 for details of the anaerobic digestion apparatus 10, pipe 8 receives raw, untreated sewage 12 which passes downwardly through feed pipe 13 into concentrically disposed compartment 30 within which the psychrophilic stage of the anaerobic process functions. This compartment 30 is bounded by heat-insulative outer wall 14 and a heat-insulative inner baffle 32. Its bottom is formed by a portion of the bottom 13 of the concrete tank 14 and by sloping surface 93 and vertical surface 94, both being heat conductive, of the underlying truncated cone containing the heat-exchange compartment 90.

As the raw sewage flows in circular directions 35 within the first compartment 30, it is acted upon by the acid-producing bacteria which decompose the substrate into sludge, supernatant, and scum which are separated by gravity and convection currents into a bottom zone, a supernatant zone 36, and a top zone, respectively. The sludge 33 is deposited at the bottom of compartment 30 in its bottom zone. Further amounts of sludge enter sidewise from the adjoining mesophilic compartment through the narrow space below the baffle 32 and between the legs 31 which support the baffle 32. This narrow space is generally about 1 inch in height. Scum rises to the surface at 34. Upon reaching the two ports 38, which are placed at a suitable height below the surface 34 and within the supernatant zone 36, the clear supernatant 39 is transferred by displacement to the next concentric compartment 40, containing the mesophilic stage of the process.

In the mesophilic compartment 40, the supernatant flows in circular directions 45 toward ports 48, which are within the supernatant zone 46, and is transferred by displacement as shown at 49 into the hemi-compartment 50 containing the thermophilic entrapment stage of the process. The mesophilic compartment 40 has the sloping metallic bottom 93, outer baffle 32, and an inner baffle 42. Baffles 32, 42 typically include about two inches of insulation. The supernatant zone 46, like the supernatant zone 36 in compartment 30, is bounded by a bottom zone having a sludge layer 43 on bottom 93 and a top zone having a surface 44. Most of the sludge in sludge layer 43 is methanobacteria, but a small portion of this sludge 43 comes as sidewardly entering slime from the adjoining entrapment portion 50 of the thermophilic compartment through a narrow space between legs 41 beneath the baffle 42, this space being preferably one inch or somewhat less in height.

The entrapment portion 50 of the thermophilic compartment has a bottom zone with sloping metal bottom 93, a supernatant zone 56, and a top zone having a surface 54. Its sides are the baffle 42 and a filter 52 which is constructed of an open-network metal structure supporting a synthetic fabric which is resistant to heat and to the weak organic and inorganic acids which are present in the slime and supernatant. This fabric has apertures of 50–100 microns in size. The surface of this fabric entraps any suspended solids larger than 50 microns in size until such time as the solids are hydrolized and metabolized or reacted by the thermophilic bacteria. The fabric also permits clear supernatant from the supernatant zone 56 to pass therethrough into the treated portion 60 of the thermophilic compartment.

In practice, the filter builds up a bacterial slime which is rich in bacteria and through which the thermophilic fluid must pass from supernatant zone 56, as shown at 59, before entering the treated portion 60 of the thermophilic compartment, so that residual biodegradable pollutant is removed. The filter 52 will not block because any heavy build-up of slime breaks away from the filter and descends to the bottom of the compartment. The deposit of slime 53 in portion 50 is, of course, much smaller in quantity than the sludge layers 43 and 33. The sidewise-moving solids, as slime 53 and sludge 43, do not block the bottoms of the baffles 42 and 32 in practice. However, short circuiting between the compartments 30, 40, 50 has also not been observed in practice, presumably because density currents emanating from the bottom 93 of the apparatus 10 rise vertically and density differentials presumably inhibit such sidewise movement.

Location of the dual exit ports 38, from the psychrophilic compartment 30 into the mesophilic compartment 40, and the location of the sidewardly separated dual ports 48, from the mesophilic compartment 40 into the thermophilic entrapment portion 50 has also produced no harmful effects as to stagnation of liquid therebetween. However, a plurality of ports 38 and 48 can be disposed between the respective compartments oppositely to the respective inlets thereto, particularly if vertically spaced in the supernatant zones 36, 46. It is particularly important that more than one port be available for movement of liquid in the event that one port becomes temporarily blocked.

The treated portion 60 of the thermophilic compartment has a surface 64 and is bounded by the filter 52, the solid support 51 beneath the filter 52, an inner wall 62, and the sloping metal bottom 93. The filtered thermophilic supernatant flows from the central zone 66 through the outlet port 68, passes downwardly through the pipe 65, and flows as shown at 69 into the bottom zone of the sterilization compartment 70.

The sterilization compartment 70 is bounded by the inner wall 62, the top 92 of the underlying heat-exchange compartment 90, and an inner lid 78 which comprises an inspection port 80 and a gas vent 75. The fluid entering the sterilization compartment 70 is heated at 92 by the sterilized fluid contained within the heat-exchange compartment 90, thereby establishing convective currents 73 within sterilization compartment 70. As the fluid rises, it is further heated by a heating means such as a hot-water coil 83 to a temperature of 82° C or greater, so that the fluid is thoroughly sterilized.

Hot water, which may be provided for the heating coil by an suitable means, enters through pipe 81, passes through the coils 83, and exits as cooled water through pipe 84. The sterilization compartment 70 may also contain a thermostat 79 connected to a means for monitoring and/or controlling the temperature within the central zone 76.

The sterilized fluid at the top of the sterilization compartment 70 flows, as shown at 74, into and downwardly through pipe 71, and is discharged as shown at 96 into the heat-exchange compartment 90 located at the bottom of the anaerobic apparatus 10. The sterilized fluid then releases heat to the psychrophilic compartment 30, the mesophilic compartment 40, the thermophilic entrapment and-treated compartment 50 and 60, and the sterilization compartment 70 as previously described.

The heat-exchange compartment 90 is shaped like a truncated cone and has a bottom formed by the outer wall 14, the annular vertical surface 94, the annular sloping surface 93, and the horizontal surface 92. The sterilized fluid exits from heat-exchange compartment 90, as shown at 98, flows upwardly through pipe 101, and exits from the anaerobic digestion apparatus 10 through pipe 21 as shown at 108. The upper part of pipe 101 is insulated by insulating means 103, and pipe 101 is open at its upper end to allow gases to escape as shown at 106.

These gases are principally methane, are produced at about 6.25 cubic feet per pound of BOD, and have a heat content of about 600 btu per cubic foot. Because the anaerobic apparatus of this invention is gas and water tight, the gas 106 can be removed at suitable vent points, stored in a gas receiver, and vented or burned as required. Preferably, however, the gas 106 is vented by a separate pipe FIG. 1 - above pipe 101 to the aerobic filter bed 110 in which the gas is oxidized to water and $CO_2$ which is discharged to the atmosphere by means of a soil vent pipe. From treatment plant back through influent sewage line to soil vent pipe.

The anaerobic apparatus 10 functions according to displacement of previously treated influent by subsequently entering influent. No deleterious effects have been noted in any anaerobic apparatus of this invention after an intermittent or "slug" loading, such as a fifty-gallon bath flush. Indeed, in an anaerobic apparatus 10 having a capacity of 700 imperial gallons, a displacement of at least 500 imperial gallons is required before any noticable effects on BOD or suspended solids can be shown, unlike present systems which show immediate effects from such a large displacement.

Hydraulic residence time in an anaerobic apparatus of the invention is three days, but this can be reduced to as little as one day at the risk of losing latitude for under-/overload conditions. Moreover, again contrary to presently used devices, underloading or lack of use for 21 days had no effect upon anaerobic apparatuses of the invention having a 3-day hydraulic residence time, because the psychrophilic stage within the first psychrophilic compartment retains a reserve food supply which continues to be digested slowly and continues to feed the bacteria therein.

The bacteria operate on a normal BOD loading of 0.009 pounds per cubic foot on an average throughput of 60 gallons per person at 0.16 pounds $BOD_5$ per person, so that the throughput from a four-person household can be suitably handled by a domestic unit having a capacity of 700 imperial gallons.

It has been found that methanobacteria are found almost exclusively in the mesophilic and thermophilic stages, that the oxygen concentration in the mesophilic stage is less than 0.08 ppm, and that all the bacterial flora are subject to rapid fluctuations in numbers from samples taken from time to time in the same apparatus and between different apparatuses.

During other tests on an apparatus 10 having no dolomite therein, the method of sampling permitted air to enter the mesophilic and thermophilic compartments of the apparatus which resulted in "stuck" digestion. Because of the death of methanobacteria, the initially low volatile acid concentration thereupon very rapidly increased to 2,000 mg/liter or more, reducing the pH to 4.5 or less.

Dolomite chips, of three/fourths-inch size, were then placed loosely at the base of the psychrophilic compartment. Because dolomite acts as a buffer for the volatile acids and also counteracts chlorine and various germicidal and bacterio-static agents, such difficulty with stuck digestion was thereafter minimized.

Although the dolomite in compartment 30 can be expected to last a considerable time, FIGS. 5 and 6 show an alternative means for adding dolomite and for exposing it to the flow of sewage within all three zones of compartment 30. Two pair of flexible plastic pipes 121, 122 and 131, 132, having slots or holes 125 therein, are placed on each side of pipe 37 and pipe 101 within compartment 30. Crushed dolomite 138 is added to each pipe 121, 122 and 131, 132 until it is filled. The pipes 121, 122 and 131, 132 can extend through and be sealably attached to the lid 15. If provided with an air-tight cap, each pipe 121, 122 and 131, 132 can be inspected at intervals for the level of dolomite 138 therewithin without introducing an appreciable amount of air into the apparatus 10.

In each of the three outer annular compartments 30, 40, 50, and 60, the supernatant zone, corresponding to what is known in the art as the water zone, consists of a laminar layer of low-density fluid. When sewage 12 is added to the apparatus 10, there is successive stage-wise displacement, and the fluid in each supernatant zone 36, 46, 56, 66 becomes somewhat compressed, compelling fluid from both sides of the ports 38, 48 to pass through them.

In the outermost annulus containing the psychrophilic stage, raw sewage receives primary treatment which initially involves removing all free oxygen, both dissolved and gaseous, that enters with the sewage 12. Although this annulus operates at a comparatively low temperature range, the increase of temperature over the entering temperature of about 60° F (15.6° C) decreases the oxygen-holding power of the fluid.

Common anaerobes of facultative nature within the psychrophilic compartment 30 commence to break down the solids into smaller particles and eventually to reduce them into a soluble form. In the process, the facultative organisms consume any remaining free oxygen, rapidly converting the system into a true anaerobic state. Starch and cellulosic materials are rapidly converted into simple types of sugar, forming acids which tend to reduce the pH when such starch and cellulose degradation is well advanced. Consequently, the presence of dolomite in the psychrophilic stage enables the organisms to continue digestion of starch and cellulosic materials until they are fully degraded. In the psychrophilic stage, fats are initially untouched because of difficulties in their complex structure, but proteins are converted into amino acids.

Because the outer wall 14 and the baffle 32 insulate the fluid within the psychrophilic compartment 30, heat is transferred almost entirely from the bottom surfaces 93, 94, and the upwardly moving convection currents form a curtain as the essentially sole means of transferring heat within the psychrophilic compartment 30. The fluid 39 passing through the holes 38 contains mainly dissolved solids and very fine settleable suspended solids which are acted upon within the mesophilic stage by highly specialized methane formers which continue to hydrolyze the fine suspended solids and the dissolved solids with intracellular enzymes to form intermediate acetates, carbon dioxide, and methane. Most of the methane produced by the anaerobic apparatus 10 of this invention is formed in the mesophilic compartment 40.

Because the cylindrical baffles 32, 42 provide adequate insulation, the fluid within the mesophilic compartment 40 receives heat almost entirely from the sloping bottom surface 93 and the upwardly moving convection currents form a curtain as almost the sole means of transferring heat upwardly within the compartment 40. The two or more holes 48 in the baffle 42, at a carefully determined height therein, permit the passing of low-density supernatant from the supernatant zone 46 of the mesophilic stage into the thermophilic stage where final digestion takes place by a different genera of highly specilized thermophilic bacteria which act upon any suspended and dissolved solids within the entrapment portion 50 and upon the slime which gathers upon the filter 52. Moreover, within the treated portion 60, these bacteria attack any remaining dissolved solids, so that any residual biodegradable pollutant is removed.

Presently used activated-sludge systems, extended-aeration trickling filters, and septic tanks cannot possibly utilize methane formers that cannot exist out of their particular pH, temperature, and dissolved-oxygen ranges, and sludge digestors operate at a normal fixed temperature of about 100° F (37° C) which similarly excludes most of the essential methane formers. The process of this invention is based upon finding that anaerobic digestive processes double in rate for each 10° C rise in temperature between 10° C and 50° C, thereby reducing the time required for digestion from six months in the lower temperature range to as little as 12 days at 60° C. Further experiments with anaerobic apparatuses constructed in accordance with the invention are as follows:

EXAMPLE I

With first three annular compartments at successively higher temperatures up to 60° C, the effluent from the last compartment was passed into the fourth compartment which was held at a temperature of 74° C for sterilizing. Although the effluent therefrom was free of Escherichia Coliform organisms, the five-day biological oxygen demand ($BOD_5$) additionally decreased; this result indicated that further biological degradation had taken place during the sterilization process. The presence of ultra-temperature thermophilic bacteria, believed to be Methanobacterium Thermoautotrophicum, was then proven by increasing the temperature a further 10° C in the fourth compartment and finding that further degradation therein had been prevented and the responsible organism had presumably been destroyed.

EXAMPLE II

In an operating anaerobic apparatus constructed according to the invention and filled with sewage being digested, supernatant was displaced from the psychrophilic compartment by adding thereto a volume of fresh sewage equalling the volume of the psychrophilic compartment and repeating the addition daily until a constantly sterile (with the possible exception of viruses which were not tested) and clear sample was repeatedly obtained from the fourth sterilization compartment, thereby proving that pollution was being removed in the anaerobic apparatus in three days instead of twelve.

EXAMPLE III

An anaerobic apparatus constructed according to the principles of this invention was connected to a machine shop occupied by 15 people working eight hours per day and daily producing 150 imperial gallons of sewage, including mineral oil. Samples were removed from the thermophilic stage and passed through a sand filter without aerating. The nitrogen compounds were almost completely removed by adding nitrites.

The results of the examination are as follows:

| Property | Finished Product | Sewage Input | % Efficiency |
|---|---|---|---|
| Dissolved Oxygen, mg/l | 3.3 | 5.0 | — |
| Temperature, ° C | Ambient | 15° C | — |
| pH | 7.1 | 6.4 | — |
| BOD, mg/l | 14 | 540 | 97.4 |
| Suspended Solids, mg/l | 26 | 160 | 83.75 |
| Ammonia-N, mg/l | 110 | — | — |
| Nitrite-N, mg/l | 0.01 | — | — |
| Nitrate-N, mg/l | 20.3 | — | — |
| Organic-N, mg/l | 4.4 | — | — |
| Phosphate, mg/l | 20.6 | — | — |
| Turbidity, J.T.U. | 15 | — | — |
| Colour, Pt/Co | 150 | — | — |
| Oil, mg/l | 11.0 | — | — |
| A.B.S., mg/l | 0.20 | — | — |
| T.D.S., mg/l | 404 | — | — |
| E. Coli I | 6,200 | — | — |

-continued

| Property | Finished Product | Sewage Input | % Efficiency |
|---|---|---|---|
| orgs/100 ml | | | |

EXAMPLE IV

An anerobic apparatus constructed according to this invention was connected to a household containing five adults with the wife home during the 5-day work week and all present during the weekend. Samples were removed from the apparatus over a 12-day period, beginning at 6:00 a.m. on the first day and one hour later on each successive day, concluding at 5:0 p.m. on the 12th day. The pH was taken with each temperature check. Over the entire 12-day period, the pH averaged 5.6 at the top of the psychrophilic compartment, 6.2 at the top of the mesophilic compartment, 7.2 at the top of the treated portion of the thermophilic compartment, and 7.4 at the top of the sterilizer compartment. There were no marked differences in pH or temperature over the weekends as compared to the weekdays, demonstrating that the units could successfully operate under "slug" loads.

The apparatus had a diameter of five feet and six inches and a water depth in its sterilizer compartment of exactly 7 feet so that it contained slightly over 1,000 imperial gallons. The temperatures were taken by suspending a thermometer in each compartment at the bottom, approximately midway, and at the top. The mean temperatures over the 12-day testing period were as follows:

| Compartment in which temperature and pH reading were taken | Temperature, ° C. |
|---|---|
| Psychrophilic compartment | |
| Bottom | 21.1 |
| Midway | 30.0 |
| Top | 41.7 |
| Mesophilic compartment | |
| Bottom | 38.3 |
| Midway | 43.9 |
| Top | 54.4 |
| Thermophilic compartment | |
| Bottom | 45.6 |
| Midway | 52.8 |
| Top | 65.2 |

EXAMPLE V

An anaerobic apparatus having the same dimensions as in Example IV was connected to a household consisting of four adults, the wife being home all day and all four being present during the weekend. Testing was performed exactly as for Example IV. The pH and temperature results were also essentially identical to the results of Example IV, and tests for pH and temperature over the weekend showed no marked differences from the weekdays.

The contents of the heat-exchange compartment 90 are thermally stratified so that the hottest temperatures are close to the flat circular area 92 and progressively cooler fluid is therebelow. Accordingly, heat is transferred from the sterilized fluid back into the sterilizing compartment 70 through its metallic cylindrical base 92. Then heat at a reduced temperature is transferred to the surrounding annulus of the thermophilic compartment 50 and 60 through its metallic bottom 93. Next, heat is transferred at a still lower temperature to the middle annulus of the mesophilic compartment 40 through its sloping metallic bottom 93. Lastly, heat is transferred as residual heat at an even lower temperature to the outer annulus of the psychrophilic compartment 30 through the sloping metallic bottom 93 and the cylindrical side 94.

In each of the three annuli 30, 40, 50, 60, heat emanating from the heat-exchange compartment 90 through surfaces 93 and 94 creates convention currents which rise through each narrow channel to the top of the fluid level, carrying in the convection currents both the bacteria and the pollutants which are intermittently mixed together in a continuous cycle, thus ensuring thorough mixing without the use of any machinery. The bottom zones, the supernatant zones 36, 46, 56, 66, and the surface zones of each compartment are not highly differentiated but are characterized by characteristically stratified thermal layers with the hottest layer being at the top of each compartment and the coolest layer being at the bottom of each compartment.

In the central sterilizing compartment 70, heat is provided by means of electric submersible elements, heated water coils 83, or any other heat-transfer means known to the art. Any heating source, such as methane gas produced in the apparatus, solar heat, electromagnetic radiation, oil burning boilers, thermal cooling systems, nuclear reactions, or any electrical or other energy source may be used to provide the heat. As the water is heated in the bottom zone of the cylindrical compartment 70, the water close to the surface 92 expands and produces localized low-density layers which arise as convection current 73 through the middle zone 76 toward the top of the fluid, creating stratified heat layers with the hotter layers being at the top of the cylinder 62.

Because the anaerobic apparatus 10 of this invention operates entirely upon displacement, the stratified heat layers remain in their stratified relationship but become gradually hotter if no displacement occurs. Accordingly, some biological degradation of soluble solids may take place in the lower portions of the compartment 70 at temperatures up to 7° C, but as the entire body of liquid within the sterilizing compartment 70 becomes hotter, the thermal layer having an initially sterilizing temperature drops lower and lower.

In designing an anaerobic apparatus 10 of this invention it is important to design the sides of the cylinder 62 to contain sufficient volume for handling and sterilizing the clarified fluid at peak flow rates because sterilization is a function of both time and temperature. If maximum flow rate is continued for sufficient time to displace substantially all of the fluid in sterilizing compartment 70 before the fluid in the top zone thereof reaches sterilizing temperature, the output 108 would not be sufficiently sterile to enter the aerobic system of this invention.

Returning to the aerobic system for receiving, oxidizing, and de-nitrifying the clear, sterilized fluid 108, the feed line 23 is connected to the boundary trap 22 and is tee-connected to a slotted or perforated pipe 114, the distal ends of which are closed and spaced about one inch from the sides of the filter bed 110, as shown in FIG. 2. The feed pipe 114 is leveled and bedded upon a three-inch thick layer of three/fourth-inch rock screenings which extend as a thin and carefully levelled bed between the feed pipe 114 and the discharge-collecting pipe 116. The rock layer 111 is covered with a barrier layer of biodegradable material, such as paper, and soil 112 is placed thereon.

The effluent leaving the anaerobic digestion apparatus 10 contains nitrogen compounds, aldehydes, and ketones, but virtually no organic pollutants, and is quite anaerobic. Upon entering the rock layer 111, the fluid percolates around the rock screenings therein, forming a very thin fluid film around each piece of rock. The space between the rock screenings contains a large volume of air which is strongly attracted by the anaerobic fluid and initially volatilizes the chemical end products contained therein, thereby removing what could not be removed in the anaerobic digestion apparatus 10 because of the lack of a suitable hydrogen acceptor.

When the volatilization process is well advanced, the effluent retains the available oxygen which it obtains in the air spaces between the rock screenings, thus providing oxygen for consumption by obligate aerobic nitrogen-fixing bacteria of the family azotobactericeae of which there are four different genera, each having specific ways of fixing and removing nitrogen as organic nitrogen, ammonia nitrogen, molecular nitrogen, or nitrate or nitrite nitrogen.

At the far end of the filter bed 110, a trough having width and depth of a slotted pipe (such as 3-½ inch pipe) is covered with a thin layer of rock screenings and the slotted pipe 116 is placed thereupon to receive and to collect the discharge from the filter bed 110. The pipe 116 is connected at one end thereof to a pipe 117 which is connected to a small concrete connection pit 118. Consequently, the discharge from the filter bed 110 is collected in the pipe 116, enters the collection pit 118 through line 117, and is then discharged through line 119 to a suitable natural waterway or to a collection point for reuse. This fluid, having passed through the anaerobic system and the aerobic system of this invention and having given up its nitrogen, is perfectly safe to discharge to waterways because weeds and other obstructing plant life cannot grow by entrophication therein.

Because it will be readily apparent to those skilled in the art that innumerable variations, modifications, applications, and extensions of these embodiments and principles can be made without departing from the spirit and scope of the invention, what is herein defined as such scope and is desired to be protected should be measured, and the invention should be limited, only by the following claims.

What is claimed is:

1. A process for treating sewage, comprising
  A. as a psychrophilic stage, flowing raw untreated sewage by gravity within a narrow and deep psychropilic compartment while:
    (1.) heating the sewage along the bottom of said psychrophilic compartment to create upward convection currents and form thermally stratified bottom, supernatant, and top zones,
    (2.) receiving transversely moving mesophilic sludge along said bottom from an adjoining narrow and deep mesophilic compartment, and
    (3.) digesting said sewage at a temperature of about 20°–45° C. to form a psychrophilic sludge and a psychrophilic supernatant;
  B. as a mesophilic stage, transferring said psychrophilic supernatant by displacement to said mesophilic compartment and flowing said psychrophilic supernatant therein while:

(1.) heating said supernatant along the bottom of the mesophilic compartment to create upward convection currents and form thermally stratified bottom, supernatant, and top zones, and (2.) receiving transversely moving bacterial slime along the bottom of said mesophilic compartment from an adjoining narrow and deep entrapment portion of a thermophilic compartment; and (3.) digesting said psychrophilic supernatant at a temperature of about 35°–55° C. to form a mesophilic supernatant and the mesophilic sludge;

C. as a thermophilic stage, transferring said mesophilic supernatant by displacement to said entrapment portion and flowing said supernatant therein while:

(1.) heating said supernatant along the bottom of said entrapment portion, to create upward convection currents and form thermally stratified bottom, supernatant, and top zones, and (2.) exposing said mesophilic supernatant to a filter which:
(a) has 50–100 micron apertures, and
(b) provides sufficient surface area for entrapping any suspended solids greater than 50 microns in size, and (3.) digesting said entrapped solids caught on said filter at a temperature of 45°–70° C until said entrapped solids are hydrolyzed and reacted by thermophilic bacteria to form said bacterial slime and a treated fluid and passing said treated fluid through said filter into an adjoining narrow and deep thermophilic treated portion along which said treated fluid flows while being heated along the bottom thereof;

D. as a sterilizing stage, transferring said treated fluid to the bottom zone of a sterilizing compartment having a bottom heat-transfer surface and a heating means;

E. heating said treated fluid from said bottom surface and with said heating means in said sterilizing compartment to a temperature above 75° C to form a sterilized treated fluid at the top of said sterilizing compartment; and F. as a heat-exchange stage, transferring said sterilized treated fluid to an underlying storage compartment, having a top area and a sloping side area, from which heat is transferred at successively decreasing temperatures from the top area to said bottom surface of said sterilizing compartment and, from said sloping side area, to said bottoms of said treated and entrapment portions of said thermophilic compartment, said mesophilic compartment, and said psychrophilic compartment.

2. The process of claim 1 wherein dolomite is provided in said psychrophilic stage for maintaining the pH of said sewage within the range of 6.0 to 7.5.

3. The process of claim 2 which further comprises oxidation and de-nitrification of said sterilized treated fluid.

4. The process of claim 3 wherein said oxidation and denitrification comprise:

A. passing said sterilized treated fluid through a means for blocking ingress of air to said storage compartment and distributing said sterilized treated fluid to a substantially horizontal area having a surface means for dispersing said fluid as a thin film and for exposing said thin film to air, whereby nitrogen in said fluid is fixed and removed by aerobic bacteria;

B. collecting said de-nitrified fluid; and

C. transferring said fluid to natural waters without harm thereto.

5. A process for treating biodegradable fluid waste, comprising:

A. as a first stage, flowing said fluid waste along a narrow and deep first compartment having a heat-conducting bottom and a means along one elongated side of said bottom for receiving a transversely-moving secondary precipitant from an adjoining narrow and deep second compartment while:

(1) heating said fluid waste along said heat-conducting bottom to create upwardly moving convection currents and form thermally stratified bottom, supernatant, and top zones;

(2) receiving said transversely moving secondary precipitant; and (3) forming a primary supernatant and a primary precipitant in combination with said secondary precipitant; and B. as a second stage, transferring said primary supernatant by displacement to said adjoining second compartment, having a sidewise-sloping, heat-conducting bottom and a means along one elongated side of said bottom for receiving transversely moving treated solids from an adjoining narrow and deep entrapment portion of a third compartment, while:

(1) heating said supernatant along said bottom of said second compartment to create upwardly moving convection currents and form thermally stratified bottom, supernatant, and top zones, (2) receiving said transversely moving treated solids along said bottom, (3) forming a secondary supernatant and said secondary precipitant in combination with said treated solids;

C. as a third stage, transferring said secondary supernatant by displacement to said entrapment portion having a sidewise-sloping, heat-conducting bottom and flowing said supernatant therein while:

(1) heating said supernatant along the bottom of said entrapment portion to create upwardly moving convection currents and form thermally stratified bottom, supernatant, and top zones, and (2) exposing said supernatant to a filter which:
(a) forms one elongated side of said entrapment portion, and
(b) provides sufficient surface area for entrapping any suspended fine solids in said supernatant, and (3) treating said supernatant and said entraped solids until said treated solids and a treated fluid are formed and passing said treated fluid through said filter into an adjoining narrow and deep treated portion, having a heat-conducting bottom, along which said treated fluid flows while being heated along the bottom thereof;

D. as a final heating stage, transferring said treated fluid to the bottom zone of a hot compartment having a bottom heat-transfer surface and a heating means while heating said treated fluid from said bottom surface and with said heating means in said hot compartment to form a hot treated fluid at the top of said central compartment;

E. as a heat-exchange stage, transferring said hot treated fluid to an underlying storage compartment, having a top area and a sloping side area, from which heat is transferred at successively decreasing temperatures from said top area to said bottom surface of said hot compartment and from said sloping side area to said bottoms of said treated and entrapment portions of said third compartment, said second compartment, and said first compartment, to form a cooled treated fluid; and F. removing said primary precipitant and said cooled treated fluid from said primary compartment and said storage compartment, respectively.

6. A process for treating a biodegradable fluid waste in successive stages, all stages employing countercurrent heat transfer and the penultimate stage being additionally heated by a heating means for adding a selected quantity of heat, comprising:

A. flowing said fluid waste, by displacement in successively opposite directions, through a series of narrow and deep compartments having:
   (1) heat-conducting bottoms,
   (2) a means along one elongated side of each said bottom, except the last thereof, for receiving transversely moving solids, and
   (3) a means along the other elongated side of each said bottom, except the first thereof, for delivering said transversely moving solids;

B. heating said fluid waste along said heat-conducting bottoms to create upwardly moving convection currents and form thermally stratified bottom, supernatant, and top zones therein;

C. treating said fluidwaste within said zones to form said solids and a supernatant in each said compartment;

D. transferring said solids sidewise to the compartment in which the preceding stage is conducted;

E. transferring said supernatant to the compartment in which the succeeding stage is conducted;

F. in said last compartment, flowing said supernatant alongside a filter bisecting said last compartment and passing treated fluid through said filter;

G. as a final heating stage, transferring said treated fluid to the bottom zone of a hot compartment having a bottom heat-transfer surface and a heating means while heating said treated fluid from said bottom surface and with said heating means in said hot compartment to form a hot treated fluid at the top of said hot compartment;

H. as a heat-exchange stage, transferring said hot treated fluid to an underlying storage compartment, having a top area and a sloping side area, from which heat is transferred at successively decreasing temperatures from said top area to said bottom surface of said hot compartment and from said sloping side area to said heat-conducting bottoms to form a cooled treated fluid; and I. removing said cooled treated fluid from said storage compartment.

7. An aerobic process for biologically treating a biodegradable fluid waste, comprising:

A. providing a purality of narrow and deep flow chambers which are adjoiningly disposed and sequentially interconnected and into the first of which said fluid waste flows to form a supernatant fluid and settled solids therein;

B. providing a plurality of fluid transfer means for said sequentially interconnecting said flow chambers and for forwardly moving said supernatant fluid being displaced by said biodegradable fluid waste entering said first flow chamber, each said fluid transfer means being disposed at the ends of said plurality of flow chambers and at mid-depth therein;

C. providing a plurality of solids transfer means for said sequentially interconnecting said plurality of flow chambers and for transversely and countercurrently moving said settled solids by gravity, said plurality of solids transfer means being disposed along the bottoms of said plurality of flow chambers;

D. heating said biodegradable fluid waste along the bottom of said first flow chamber to create upward convection currents and form thermally stratified bottom, supernatant, and top zones therein, said supernatant fluid being heated and disposed within said supernatant zone;

E. transversely and countercurrently receiving said settled solids along said bottom of said first flow chamber through one of said plurality of solids transfer means;

F. forwardly and sequentially flowing said supernatant fluid into all of the remaining flow chambers of said plurality thereof while transversely and countercurrently receiving said settled solids in all but the last of said remaining flow chambers;

G. in said last of said remaining flow chambers, providing a filter means for entrapping suspended particles, for enabling thermophilic bacteria to digest the entrapped particles, and for permitting a clear fluid to pass therethrough;

H. flowing said clear fluid out of said last of said remaining flow chambers and providing a sterilizing means for heating said clear fluid to temperatures above 75° C to form a sterilized fluid;

I. providing a heat-exchange means for countercurrently transferring heat from said sterilized fluid to said sterilizing means and to said plurality of flow chambers to form a cooled sterilized fluid.

8. The process of claim 7 wherein said cooled sterilized fluid flows through a trap means for excluding air from said heat-exchange means and is anaerobically treated to produce a de-nitrified fluid.

* * * * *